United States Patent [19]

Burbidge et al.

[11] 4,192,771

[45] Mar. 11, 1980

[54] PROCESS FOR DISPERSAL AND REDISPERSAL OF PLATINUM GROUP METALS COMPRISING SULPHIDING IN A STREAM OF INERT GAS

[75] Inventors: Bernard W. Burbidge, Leatherhead, England; David M. Rees, Swansea, Wales

[73] Assignee: The British Petroleum Company Limited, Sunbury-on-Thames, England

[21] Appl. No.: 901,789

[22] Filed: May 1, 1978

[30] Foreign Application Priority Data

May 4, 1977 [GB] United Kingdom ............... 18648/77

[51] Int. Cl.$^2$ ...................... B01J 37/20; B01J 37/24; B01J 23/40; B01J 23/96
[52] U.S. Cl. ..................................... 252/415; 208/138; 208/139; 208/140; 252/411 R; 252/419; 252/439; 252/466 PT; 252/472; 585/482
[58] Field of Search .................... 252/411 R, 415, 416, 252/419, 439, 466 PT; 208/138, 139, 140; 260/668 A

[56] References Cited

U.S. PATENT DOCUMENTS

| | | | |
|---|---|---|---|
| 2,880,161 | 3/1959 | Moore et al. | 208/140 |
| 3,660,271 | 5/1972 | Keith | 208/139 |
| 3,838,039 | 9/1974 | Vesely et al. | 208/140 |
| 3,953,368 | 4/1976 | Sinfelt | 252/466 PT |
| 3,981,823 | 9/1976 | Yates | 252/415 |
| 4,046,671 | 9/1977 | Burbidge et al. | 252/415 |

FOREIGN PATENT DOCUMENTS 49-33749  9/1974  Japan ...................... 252/415

Primary Examiner—P. E. Konopka
Attorney, Agent, or Firm—Morgan, Finnegan, Pine, Foley & Lee

[57] ABSTRACT

A process for the redispersal or dispersal of a platinum group metal in a catalyst comprising an oxidized platinum group metal component and a refractory inorganic support comprises the steps of treating the oxidized catalyst with a stream of inert gas containing a sulphiding agent and reducing the sulphided catalyst in a stream of hydrogen-containing gas at a temperature in the range 200° to 600° C. to give a maximum catalyst temperature of 550° C.

10 Claims, 1 Drawing Figure

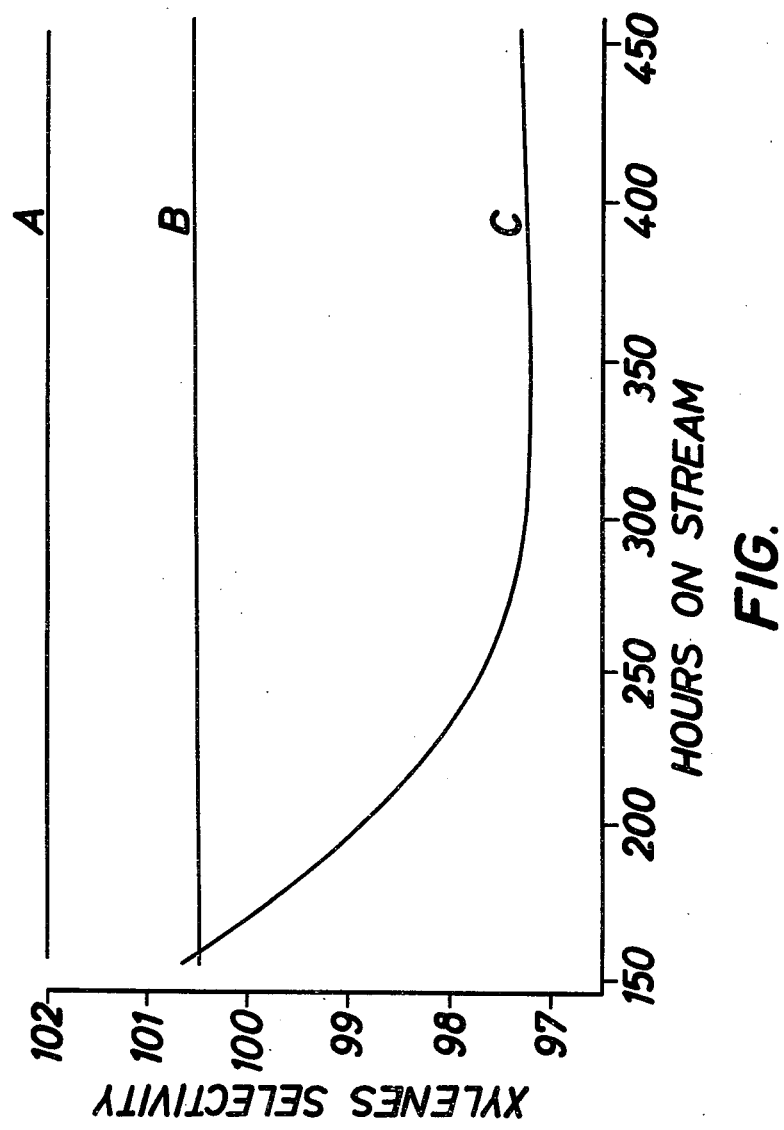

PROCESS FOR DISPERSAL AND REDISPERSAL OF PLATINUM GROUP METALS COMPRISING SULPHIDING IN A STREAM OF INERT GAS

The present invention relates to the treatment of platinum group metal catalysts to improve their activity and/or selectivity, and more particularly to the treatment of hydroconversion catalysts comprising a platinum group metal supported on a refractory inorganic support.

Numerous hydrocarbon conversion processes are known in the petroleum industry which employ platinum group metal catalysts. These include, for example, reforming, low temperature isomerisation of n-paraffins, isomerisation of alkyl aromatics and selective wax hydrocracking. In use, carbonaceous and possibly other deposits form on the catalysts and reduce their activity.

The regeneration of such catalysts by oxidative burn off and subsequent reduction is generally known, but in practice, difficulties have been experienced. For example, with catalysts of a platinum group metal on a refractory oxide support, initial or near initial activity can be resorted by regeneration but this restored initial activity is not always maintained over long periods of further operation. This failure to restore sustained activity appears to be related to the regeneration itself rather than to non-reversible loss of activity during processing, because a relatively fresh, active catalyst can itself lose activity as a result of regeneration.

The present invention is based on the belief that low activity is usually due to agglomeration of the platinum group metal during regeneration and this invention proposes a treatment to redisperse the platinum group metal, by converting the oxidised metal to sulphide prior to reduction instead of reducing directly after oxidation as is conventional practice. The treatment is also applicable to fresh catalyst when this is supplied in an oxidised form.

Thus according to the present invention there is provided a process for the redispersal or dispersal of a platinum group metal on a catalyst comprising an oxidised platinum group metal component and a refractory inorganic support, which process comprises the steps of treating the oxidised catalyst with a stream of inert gas contaning a sulphiding agent, and reducing the sulphided catalyst in a stream of hydrogen-containing gas at a temperature in the range 200° to 600° C. to give a maximum catalyst temperature of 550° C.

If the catalyst has become deactivated by deposition of carbonaceous material during processing, it may be brought to an oxidised state by treating the catalyst with a stream of inert gas and free oxygen at a temperature controlled to a maximum of 550° C. The catalyst is finally purged to remove residual oxygen.

If necessary, to aid in the redispersal or dispersal the platinum group metal after treatment with oxygen, the catalyst may be treated at 400° to 550° C. with a stream of an inert gas containing from 0.1 to 20% volume of free oxygen, from 20 to 20,000 ppm of water and from 5 to 500 ppm volume of chlorine in a chlorine-containing material. The final purge step then in addition removes residual chlorine.

Describing the oxidation sequence in more detail, when the catalyst has become deactivated during a processing step utilising hydrogen, the step is terminated by stopping the flow of feedstock. The temperature at this stage may be from ambient to 450° C. and the pressure from atmospheric to the operating pressure of the process.

The aim of the oxidative treatment is to remove carbonaceous and other deposits, if present, and to oxidise the platinum group metal with agglomeration or migration of the latter kept to a minimum. The oxidation may be initiated at 100° C. or above by introducing a small amount of oxygen, preferably as air, into the inert gas. The amount of oxygen is controlled in known manner to give a maximum temperature below 550° C. The oxygen content may be from 0.1 to 20% volume with lower amounts, e.g. 0.1 to 10% volume, being used in the initial stages and larger amounts, e.g. 2 to 20% volume, being used in the later stages.

Pressure throughout the oxidation may be from 1 to 70 bars with a preference for moderate pressures of from 2 to 25 bars. The total time will depend on the amount of the deposits but may conveniently be from 20 to 200 hours, with from 10 to 100 hours at the higher temperature.

The preferred temperature for the chlorination step is 490° to 530° C. The oxygen content of the gas is not critical and may conveniently be from 0.1 to 20% volume. Concentrations between 1 and 5% are preferred. After any necessary adjustment of temperature and oxygen content the step may be initiated by adding a chlorinating agent to the gas. The concentration of chlorine in the gas is preferably from 20 to 300 ppm volume and the total amount of chlorine by weight of catalyst treated may be from 0.1 to 10% by weight, preferably from 0.2 to 5% by weight.

The chlorine can conveniently be added as chlorine gas, hydrogen chloride, or, preferably an organic chlorine containing compound, particularly a chlorinated derivative of a $C_{1-4}$ hydrocarbon. Examples of suitable compounds are carbon tetrachloride and propylene dichloride, preference being given to compounds which are liquid at ambient temperature since controlled injection of the chlorine into the gas is thereby facilitated.

Pressure may be as for the burn-off and the time may be from 1 to 36 hours.

Following the treatment with chlorine, there may be a "smoothing" step, when the injection of chlorine is stopped but operation continued at the same oxygen concentration and the same or reduced temperature. This step serves to remove any excess chlorine and the time may conveniently be from 1 to 48 hours.

After the halogenation, a conventional purge with an inert gas is given to remove the oxygen prior to the introduction of the sulphiding agent. Suitable purge conditions may be temperatures from ambient to 500° C. and pressures from atmospheric to 20 bars. Conveniently the catalyst is purged hot and preferably for the minimum time required to free the system of oxygen. The purging procedure can include an evacuation step.

The sulphide may suitably be added in the form of hydrogen sulphide, ammonium sulphide, carbon disulphide or an organic sulphur-containing compound, e.g., a mercaptan or sulphide.

The sulphur compound is conveniently added in a stream of inert gas, preferably nitrogen. This inert gas must be free from oxygen and should also initially be free from hydrogen. The concentration of sulphur in the gas is suitably from 5 to 10,000 ppm and the total amount of sulphide deposited on the catalyst may be in the range 0.01 to 1% by weight.

The sulphiding temperature may be from ambient to 500° C., preferably from 250° to 450° C. Pressure and time may be as for the purge steps.

Before the reduction step the system may be again purged, suitably with nitrogen, to remove residual sulphide.

The reduction is preferably carried out in a stream containing hydrogen flowing at 200 to 6,000 volumes of gas/volume of catalyst/hour at a final temperature of 350° to 550° C., and a pressure of atmospheric to 35 bars (ga). The time may be from 1 to 100 hours.

A suitable and convenient reducing gas is catalytic reformer off-gas.

The amount of platinum group metal on the catalyst may be from 0.1 to 10% by weight, preferably 0.1 to 5% weight. The platinum group metals are platinum, palladium, rhodium, ruthenium, osmium and iridium, the first two being preferred.

In addition to the platinum group metal, a second or more platinum group metal(s) and/or another metal or metals may also be present. Thus the process is applicable to bi-metallic and multi-metallic catalysts, particularly those containing rhenium.

The refractory inorganic support may be a refractory oxide of an element of Groups II, III or IV of the Periodic Table, e.g., silica, alumina, silica-alumina, bauxite, or a silicate, e.g., a zeolite or sepiolite.

By virtue of the sulphide treatment stage it is possible to produce a catalyst having a smaller average platinum group metal crystalline size than would otherwise be the case. This results in a catalyst of restored or enhanced activity and/or selectivity.

The above method of treatment is particularly suitable for improving catalysts intended for use in the isomerisation, disproportionation and/or dealkylation of alkyl aromatic hydrocarbons.

Thus according to another aspect of the present invention there is provided a process for the hydrocatalytic treatment of a mixture of $C_8$ or $C_9$ alkyl aromatic hydrocarbons which process comprises contacting the mixture under isomerisation and/or disproportionation conditions and in the presence of hydrogen with a catalyst comprising a platinum group metal on a refractory inorganic support treated as hereinbefore described, and recovering a product containing isomerised polymethyl benzenes and/or a reduced content of ethyl or propyl benzene.

Suitably the temperature is in the range from 350° to 480° C. and the pressure in the range from 0 to 100 bars (ga). The space velocity may be in the range from 0.1 to 15 v/v/hr, preferably from 0.5 to 5 v/v/hr and the hydrogen/hydrocarbon mole ratio in the range from 1:1 to 20:1, preferably from 2:1 to 8:1.

The preferred temperature is in the range from 350° to 430° C. Increase of temperature reduces the conversion of ethyl and propyl benzene and above 430° C. the extent of xylene disproportionation occurring will give an increasing loss of xylenes. The preferred pressure is in the range from 10 to 40 bars. Increasing pressure increases ethyl and propyl benzene conversion.

The preferred feedstock is a $C_8$ fraction containing one or more xylenes and ethyl benzene.

Preferably the xylene or xylenes are isomerised to substantially equilibrium proportions at the temperature used.

The amount of ethyl or propyl benzene to be converted and the amount of xylene conversion that can be tolerated will depend on particular circumstances and the optimum process conditions and conversion can readily be determined in any particular situation by experiment.

The above method of treatment is also particularly suitable for catalytic reforming catalysts.

Thus according to another aspect of the present invention there is provided a process for the catalytic reforming of a hydrocarbon fraction boiling in the temperature range 15° to 250° C. which process comprises contacting the fraction under reforming conditions with a catalyst comprising a platinum group metal on a refractory inorganic support treated as hereinbefore described.

Suitable reforming conditions include a temperature in the range 300° to 600° C., a pressure in the range 1 to 70 bars (ga), a space velocity in the range 0.1 to 5 v/v/hr and a hydrogen:hydrocarbon mole ratio in the range 0.1:1 to 20:1.

The invention is illustrated with reference to the following Examples and the Figure accompanying the Provisional Specification. Examples 1, 2, 3 and 8 are provided for purposes of comparison only and are not in accordance with the invention.

EXAMPLE 1

A charge of a commercially available Pt on silica-alumina catalyst with properties as in Table 1 was run in a commercial unit for 6 cycles giving a total catalyst life of 92 barrels per pound. A conventional oxidative regeneration was carried out at the end of each cycle to remove carbonaceous material and restore activity. Cycle lives gradually declined until, following the 6th cycle, the catalyst was deemed uneconomic to use and following regeneration was discharged. Analysis of the regenerated spent catalyst is shown in Table 1.

Table 1

| Catalyst | Type | Average Platinum Crystal Size A |
| --- | --- | --- |
| Fresh | Platinum/silica-alumina | <20 |
| Spent | Platinum/silica-alumina | 50 (93% metallic Pt) |

This shows the deterioration in catalyst performance due to platinum agglomeration.

EXAMPLE 2

A 300 g sample of regenerated spent catalyst from Example 1 was placed in a pilot plant reactor and subjected to removal of residual carbon and chlorination, as follows. After purging the reactor with nitrogen a nitrogen pressure of 3.5 bar (ga) and a recycle rate of 1,000 v/v/hr were established. Temperature was gradually raised to 400° C. when air was added to the circulating $N_2$ to give 1 to 2% $O_2$ at the reactor inlet. The temperature was gradually increased to 510° C. with air injected as necessary to maintain 1 to 2% $O_2$. Substantially all the carbon was removed over this period. The oxygen content of the nitrogen was increased to about 5% volume and the catalyst halogenated by including ca 2,000 ppm volume water vapour and 200 ppm carbon tetrachloride in the circulating nitrogen until 3.6% by weight on catalyst of chlorine had been passed.

Following sampling the treated catalyst was split into 4 equal portions for reduction studies. Analysis of the treated catalyst is give in Table 2.

Table 2

| Catalyst | Average Platinum Crystal Size Å |
|---|---|
| Rejuvenated Spent | Small amount (ca 10%) of residual metallic platinum with average size >50A |

This shows that halogen treatment under oxidising conditions changes metallic platinum to an oxidised species.

EXAMPLE 3

A 50 g sample of rejuvenated spent catalyst from Example 2 was placed in a pilot plant reactor and subjected to reduction according to the catalyst manufacturer's procedure. Following purging with nitrogen then hydrogen a hydrogen pressure of 12 bar (ga) and a recycle rate of 1,000 v/v/hr were established. The temperature was gradually increased to 482° C. and maintained for 2 hours. A similar run was carried out with a sample of fresh catalyst. Identical runs were then carried out to assess the repeatability. Analysis of the treated catalysts are given in Table 3.

Table 3

| Run | Catalyst | Average Platinum Crystal Size Å |
|---|---|---|
| 1 | Rejuvenated Spent | 29 |
|   | Fresh | <20 |
| 2 | Rejuvenated Spent | 29 |
|   | Fresh | <20 |

This shows that rejuvenation and conventional reduction were not wholly effective in restoring the platinum dispersion to that found on fresh catalyst.

EXAMPLE 4

A further 50 g sample of rejuvenated spent catalyst from Example 2 was placed in a pilot plant reactor and heated to 370° C. under 3.5 bar (ga) nitrogen containing 1 to 2% oxygen with a gas recycle rate of 1,000 v/v/hr. Following purging with nitrogen a gaseous mixture of $N_2$ and $H_2S$ was introduced to give 0.1% weight sulphur on catalyst and 3.5 bar (ga) pressure. The mixture was recycled for 2 hours at 370° C. then cooled back to 200° C. Following purging with hydrogen a reduction according to the method used in Example 3 was carried out. A similar run was carried out with a sample of fresh catalyst. Identical runs were then carried out to assess the repeatability. Analysis of the treated catalysts are given in Table 4.

Table 4

| Run | Catalyst | Average Platinum Crystal Size Å |
|---|---|---|
| 1 | Rejuvenated Spent | <20 |
|   | Fresh | <20 |
| 2 | Rejuvenated Spent | <20 |
|   | Fresh | <20 |

This shows the method of the invention has enabled the degree of platinum dispersion found on fresh catalyst to be achieved.

EXAMPLE 5

To demonstrate the effectiveness of redispersing the platinum by the method of the invention the treated catalyst from Run 2 of Example 4 was used to isomerise a commercially derived xylenes mixture depleted in orthoand para-xylenes (commonly termed mother liquor). The composition of the feedstock is given in Table 5. The process was operated at 12 bar (ga), with high purity hydrogen make-up gas, 5.0 hydrogen/hydrocarbon molar ratio, 1.33 liters of feed per liter of catalyst and reactor temperature of 427° C. Comparative data were obtained by using the fresh and regenerated spent catalysts from Example 1 in an identical manner.

Results of these tests are shown in Table 5. Xylenes selectivity is defined as the ratio of total xylenes in the product to the total xylenes in the feed (based on weight) expressed as a percentage.

The FIGURE shows that the catalyst treated by the method of the invention (line A) considerably improves the total quantity of xylenes produced from a given quantity of feed to the untreated catalyst (i.e. regenerated spent—line C) and in fact surpasses the performance of fresh catalyst (line B).

Table 5

| Feedstock Analysis | | |
|---|---|---|
| Paraffins and naphthenes | % wt | 3.61 |
| Toluene | % wt | 0.95 |
| Ethyl benzene | % wt | 22.47 |
| Para-xylene | % wt | 9.60 |
| Meta-xylene | % wt | 58.67 |
| Ortho-xylene | % wt | 4.70 |

EXAMPLE 6

A sample of a commercial reforming catalyst in the form of 1/16 inch alumina extrudates supporting platinum and rhenium, each at 0.3% weight/weight, was placed in a pilot plant reactor and pressured to 3.5 bar (ga) with a blend of oxygen and nitrogen containing 5% oxygen. A recycle gas rate of 1,000 v/v/hr was established and the reactor temperature was slowly raised to 370° C.

Following depressuring and purging with nitrogen at 370° C., the plant was repressured to 6 bar (ga) with a blend of hydrogen sulphide and nitrogen containing 1% hydrogen sulphide. This gas mixture was recycled at a rate of 1,000 v/v/hr for 2 hours to deposit sulphur on the catalyst to a level of 0.05% weight. Following depressuring and purging with hydrogen the catalyst was reduced in a hydrogen atmosphere at 14 bar (ga), 482° C. and a recycle rate of 1,000 v/v/hr for 2 hours.

The catalyst performance was evaluated in a pilot plant at selected average catalyst bed temperatures in the range 485° to 515° C. using as feedstock a medium naphthenic straight run benzine of nominal boiling range 70° to 150° C. derived from a mixture of Kuwait and Nigerian crudes. The feed had the following PNA analysis.

| Paraffins | % wt | : | 51.7 |
|---|---|---|---|
| Naphthenes | % wt | : | 34.9 |
| Aromatics | % wt | : | 13.4 |

Fixed processing conditions were as follows:

| Pressure bar (ga) | : | 34.5 |
|---|---|---|
| LHSV v/v/hr | : | 2.0 |
| Hydrogen:hydrocarbon mole ratio | : | 5.0 |
| Recycle gas water content ppm vol | : | 15-20 |

-continued

| Feed chloride content ppm wt | : | 1-2 |

The following results were obtained:

Table 6

| Average Catalyst Bed Temperature °C. | $C_5^+$ Liquid Product Yield % | RON |
| --- | --- | --- |
| 487 | 84.0 | 92.2 |
| 197 | 80.1 | 96.2 |
| 512 | 76.2 | 100.0 |
| 487 | 86.9 | 90.8 |

EXAMPLE 8

A further sample of the catalyst of Example 6 was placed in the reactor and also pressured to 3.5 bar (ga) with the blend of oxygen and nitrogen containing 5% oxygen.

Following depressuring and purging with nitrogen and then hydrogen at 370° C., the plant was pressured to 14 bar (ga) with 100% hydrogen and the reactor temperature was slowly raised to 482° C. The catalyst was reduced for 2 hours and the reactor then cooled back to 370° C. Sufficient carbon disulphide was then introduced into the recycle gas to deposit sulphur on the catalyst to a level of 0.05% weight.

The resulting catalyst was then tested as described in Example 7 with the following results:

Table 7

| Average Catalyst Bed Temperature °C. | $C_5^+$ Liquid Product Yield % | RON |
| --- | --- | --- |
| 478 | 86.4 | 88.1 |
| 488 | 84.0 | 91.3 |
| 495 | 81.2 | 95.1 |
| 505 | 76.9 | 98.3 |
| 487 | 84.9 | 90.5 |

The important runs for assessing performance are the return to low severity immediately following operation at high severity. By plotting the data given in Tables 6 and 7 it can be shown that the liquid yield at a given octane number was 2% higher than at the same temperature initially and that operation at low severity immediately following operation at high severity produced no net increase in liquid yield compared with initial operation at the same octane number.

The sulphiding of a platinum-rhenium catalytic reforming catalyst in an inert atmosphere prior to reduction is thus shown to be as effective in preventing excess initial hydrocracking as sulphiding in a reducing atmosphere following reduction. The pre-reduction sulphiding technique gave an increase of approximately 2% in reforming yield compared with the post-reduction sulphiding technique on return to low severity after high severity operation with no apparent ill effect upon the catalyst life.

We claim:

1. A method for the redispersal or dispersal of a platinum group metal on a catalyst comprising an oxidised platinum group metal component and a refractory inorganic support, which method comprises the steps of treating the oxidised catalyst with a stream of inert gas containing a sulphiding agent to deposit sulphide on the catalyst in the range of 0.1 to 1% by weight of the catalyst, and reducing the sulphided catalyst in a stream of hydrogen-containing gas at a temperature in the range 200° to 600° C. to give a maximum catalyst temperature of 550° C. at a gas hourly space velocity of 200 to 6000 v/v/hr. to produce a catalyst having an average platinum group metal crystalline size of less than 20Å.

2. A method according to claim 1 wherein the catalyst is oxidised by treating with a stream of inert gas and free oxygen at a temperature controlled to a maximum of 550° C.

3. A method according to claim 2 wherein after treatment with the stream of inert gas and free oxygen, the catalyst is treated at 400° to 550° C. with a stream of an inert gas containing from 0.1 to 20% by volume of free oxygen, from 20 to 20,000 ppm of water and from 5 to 500 ppm of chlorine in a chlorine-containing material.

4. A method according to claim 3 wherein the chlorine containing material is chlorine, hydrogen chloride or a chlorinated derivative of a $C_{1-4}$ hydrocarbon.

5. A method according to claims 1, 2, 3 or 4 wherein the sulphiding agent is hydrogen sulphide, ammonium sulphide, carbon disulphide, a mercaptan or an organic sulphide.

6. A method according to claims 1, 2, 3 or 4 wherein the concentration of sulphur as sulphide in the inert gas is in the range 5 to 10,000 ppm.

7. A method according to claims 1, 2, 3, or 4 wherein the treatment with the sulphiding agent is effected at a temperature in the range ambient to 500° C. and a pressure in the range from atmospheric to 50 bars (ga).

8. A method according to claim 7 wherein the treatment temperature is in the range 250° to 450° C.

9. A method according to claim 1 wherein the sulphided catalyst is reduced in a stream of hydrogen containing gas at a temperature in the range 350° to 550° C., a pressure in the range atmospheric to 35 bars (ga).

10. A method according to claim 9 wherein the hydrogen containing gas is catalytic reformer off-gas.

* * * * *